(12) United States Patent
Vija et al.

(10) Patent No.: US 11,790,526 B2
(45) Date of Patent: Oct. 17, 2023

(54) NEURAL NETWORK-ASSISTED DOSE ASSESSMENT BASED ON ACTIVITY IMAGE

(71) Applicant: Siemens Medical Solutions USA, Inc., Malvern, PA (US)

(72) Inventors: Alexander Hans Vija, Evanston, IL (US); Maximilian Reymann, Erlangen (DE)

(73) Assignee: Siemens Medical Solutions USA, Inc., Malvern, PA (US)

( * ) Notice: Subject to any disclaimer, the term of this patent is extended or adjusted under 35 U.S.C. 154(b) by 288 days.

(21) Appl. No.: 17/301,077

(22) Filed: Mar. 24, 2021

(65) Prior Publication Data

US 2022/0309650 A1 Sep. 29, 2022

(51) Int. Cl.
G06T 7/00 (2017.01)
(52) U.S. Cl.
CPC .. G06T 7/0012 (2013.01); *G06T 2207/10108* (2013.01); *G06T 2207/20081* (2013.01); *G06T 2207/20084* (2013.01); *G06T 2207/30004* (2013.01)
(58) Field of Classification Search
CPC ......... G06T 7/0012; G06T 2207/10108; G06T 2207/20081; G06T 2207/20084; G06T 2207/30004; A61B 6/481; A61B 6/486; A61B 6/5205; A61B 6/5217; A61B 6/037
See application file for complete search history.

(56) References Cited

U.S. PATENT DOCUMENTS

2018/0300907 A1* 10/2018 Ding .................... G06T 11/006
2020/0320753 A1 10/2020 Feng

OTHER PUBLICATIONS

Angelis, G. I., et al. "Denoising non-steady state dynamic PET data using a feed-forward neural network." Physics in Medicine & Biology 66.3 (2021): 034001.
Xu, Jinmin, and Huafeng Liu. "Deep-learning-based separation of a mixture of dual-tracer single-acquisition PET signals with equal half-Lives: A simulation study." IEEE Transactions on Radiation and Plasma Medical Sciences 3.6 (2019): 649-659.
Lee, Sun Lee at al., "Deep-dose: a voxel dose estimation method using deep convolutional neural network for personalized internal dosimetry", Scientific Reports, (2019), vol. 9:10308, https://doi.org/10.1038/s41598-019-46620-7, (pp. 1-9, 9 total pages).
Jackson, Price A. et al., "Radiation Dosimetry in $^{177}$Lu-PSMA-617 Therapy Using a Single Posttreatment SPECT/CT Scan: A Novel Methodology to Generate Time- and Tissue-Specific Dose Factors", The Journal of Nuclear Medicine, vol. 61, No. 7, Jul. 2020, DOI: 10.2967/jnumed.119.233411, (pp. 1030-1036, 7 total pages).
Trask, Andrew et al., "Neural Aritthmetic Logic Units", arXiv:1808.0058v1, [cs.NE], Aug. 1, 2018, 15 pages.
(Continued)

*Primary Examiner* — Siamak Harandi (57) ABSTRACT

A system and method includes acquisition of a plurality of images, each of the plurality of images representing radiotracer concentration in a respective volume at a respective time period, and training of a neural network, based on the plurality of images, to output data indicative of radiation dose associated with a first volume over a first time period based on a first image representing radiotracer concentration in the first volume over a second time period, the second time period being shorter than the first time period.

16 Claims, 7 Drawing Sheets

(56) References Cited

OTHER PUBLICATIONS

Barnard, E. et al., "Extrapolation and Interpolation in Neural Network Classifiers", IEEE Control Systems Magazine, Oct. 1992, (pp. 50-53, 4 total pages).
Sahoo, Subham S. et al., "Learning Equations for Extrapolation and Control", Proceedings of the 35th International Conference on Machine Learning, arXiv:1806.07259v1, [cs.LG], Jun. 19, 2018, 9 pages.
Shen, Chenyang et al., "Intelligent Inverse Treatment Planning via Deep Reinforcement Learning, a Proof-of-Principle Study in High Dose-rate Brachytherapy for Cervical Cancer", Phys Med Biol., vol. 64, No. 11, 115013, Author Manuscript, May 29, 2020, doi:10.1088/1361-6560/ab18bf, 31 pages.
Ardizzone, Lynton et al., "Analyzing Inverse Problems With Invertible Neural Networks", Publish as a Conference Paper at ICLR 2019, arXiv:1808.04730v3, [cs.LG], Feb. 6, 2019, (pp. 1-20, 20 total pages).
Resat, Haluk et al., "Kinetic Modeling of Biological Systems", NIH-PA Author Manuscript, Methods Mol Biol., 2009, vol. 541, doi:10.1007/978-1-59745-243-4_14, (pp. 311-335, 19 total pages).

\* cited by examiner

NEURAL NETWORK-ASSISTED DOSE ASSESSMENT BASED ON ACTIVITY IMAGE

BACKGROUND

Nuclear imaging modalities such as single-photon emission computed tomography (SPECT) and positron emission tomography (PET) rely on the presence of a radioactive tracer within the imaged volume. In cases where the volume is patient tissue, it is desirable to assess the radiation dose to which tissue is subjected due to the radioactive tracer. This assessment typically requires precise knowledge of the injected dose and the acquisition of tomographic quantitative images of the radioactivity, or activity, at various time points after injection of the radioactive tracer.

Activity images acquired at various time points (e.g., 0.5 hrs, 4 hrs, 24 hrs, 48 hrs) may be used to generate a time-activity curve for each sub-volume of interest (e.g., specific organs). The dose per sub-volume may then be estimated from the time-activity curves using various reconstruction techniques. Generally, the accuracy of the curves and the resulting estimates improves as the number of image acquisitions increases.

Each image acquisition consumes time and resources. Holding a patient at an imaging site between image acquisitions involves further costs and patient inconvenience. The patient may instead be released and requested to return for a next image acquisition, which raises compliance issues particularly if multiple round-trips are required. Systems are desired to facilitate spatial dose assessment based on a limited number of image acquisitions.

DETAILED DESCRIPTION

The following description is provided to enable any person in the art to make and use the described embodiments and sets forth the best mode contemplated for carrying out the described embodiments. Various modifications, however, will remain apparent to those in the art.

Some embodiments facilitate estimation of a radiation dose based on one activity image. According to some embodiments, a neural network is trained to extrapolate a dose from an activity image based on the underlying differential equations representing biological processes. Such a neural network may utilize Neural Arithmetic Logic Units (NALUs) to perform systematic numerical extrapolation by represent numerical quantities as linear activations which are manipulated using primitive arithmetic operators and controlled by learned gates.

According to some embodiments, a neural network is trained to infer one or more time-activity curves based on an activity image, and doses are estimated based on the time-activity curves. Such a neural network may determine an optimal fitting function and associated parameters for a time activity curve based on one activity image. The function and parameters may be learned in some embodiments via reinforcement learning. Some embodiments use invertible neural networks to model the estimation of a time activity curve.

Neural network performance may suffer due to a lack of adequate training data. Some embodiments utilize training data from multiple imaging sites (e.g., hospitals) to train a single neural network. Each of such imaging sites, as well as other imaging systems which did not provide training data, may then utilize the thusly-trained neural network (e.g., by downloading the trained network or accessing a cloud service for providing inferences using the trained network) to estimate dose based on an acquired activity image. The submission of training data and training of the neural network may be ongoing in order to regularly improve the performance of the trained network.

Figure 1A:
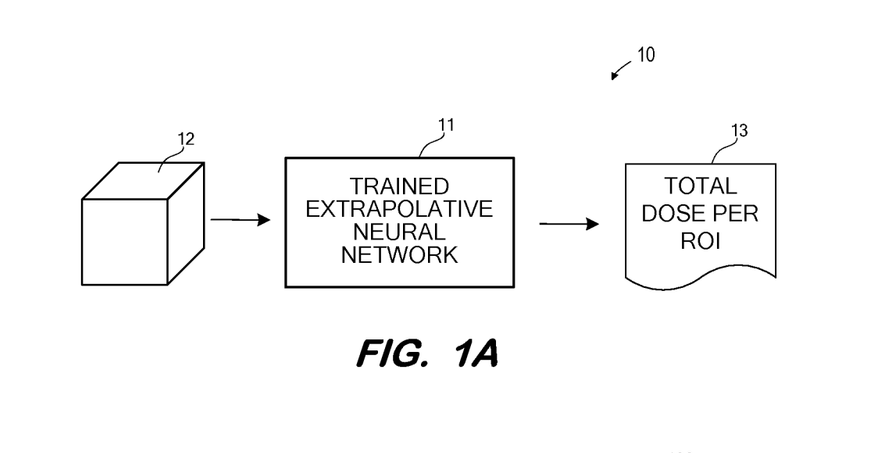
FIG. 1A is a block diagram of a system deploying a trained neural network to facilitate determination of dose distribution based on a radioactivity image according to some embodiments.

FIG. 1 illustrates system 10 to generate data indicative of radiation dose associated with a volume over a time period according to some embodiments. System 10 includes trained extrapolative neural network 11, which receives activity image 12 as input and outputs (or, infers) data 13 indicating a total dose per region of interest (ROI).

Trained extrapolative neural network 11 may be implemented using any suitable combination of hardware and/or software, and may be located remote from an imaging system by which image 12 was acquired. Network 11 may utilize NALUs to facilitate learning of its inference operation as described above. Training of a network such as network 11 according to some embodiments will be described in detail below.

Network 11, and all neural networks described herein, may comprise any type of neural network that is or becomes known. A learning neural generally consists of neurons which receive input, change internal state according to that input, and produce output depending on the input and internal state. The output of certain neurons is connected to the input of other neurons to form a directed and weighted graph. The weights as well as the functions that compute the internal state can be modified via training as will be described below. Examples of neural networks include but are not limited to convolutional neural networks, recurrent neural networks, long short-term memory networks, deep reservoir computing and deep echo state networks, deep belief networks, and deep stacking networks.

Activity image 12 may comprise a three-dimensional image reconstructed from two-dimensional projection images of radioactivity within a patient as is known in the art. For example, a radioactive tracer is injected into the patient and a set of projection images are acquired from different angles around the patient over a period of time using a nuclear imaging system (e.g., a SPECT imaging system). Each projection image indicates a degree of radioactivity (e.g., via pixel brightness) emitted from various spatial locations of the patient. Three-dimensional activity image 12 may be reconstructed from the projection images, using any reconstruction technique that is or becomes known (including neural network-assisted reconstruction), to indicate a degree of radioactivity per volume. Embodiments may employ any imaging system which produces quantitative activity data (e.g., activity measurement in Bq/ml in-situ at location (r, t)).

According to some embodiments, and depending upon the training data used to train neural network 11, network 11 may receive other input in addition to activity image 12. For example, if each training example of the training data included a type of radioactive tracer and anatomical segmentation information, neural network 11 would receive an identifier of a radioactive tracer used to generate activity image 12 and anatomical segmentation information along with activity image 12. In some embodiments, neural network 11 receives projection images of radioactivity instead of or in addition to three-dimensional image 12 reconstructed from such projection images. Embodiments are not limited to these examples of inputs.

Figure 1B:
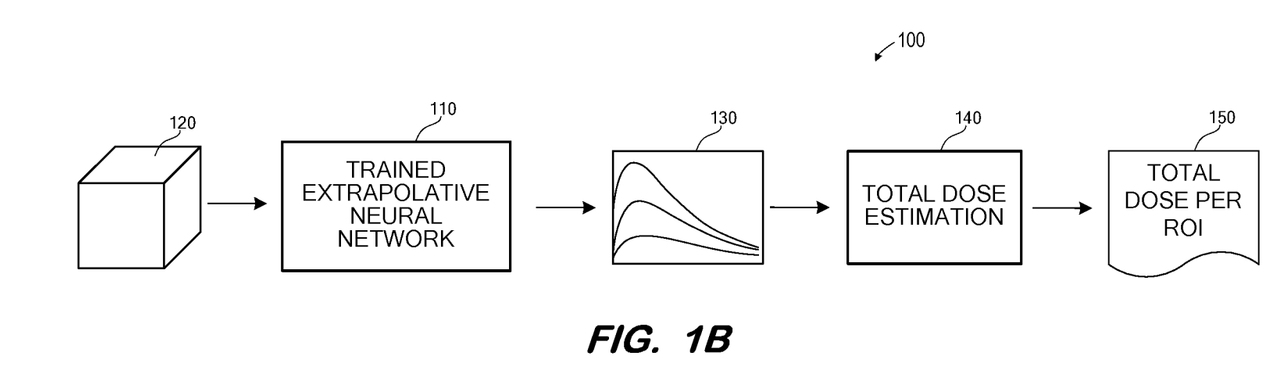
FIG. 1B is a block diagram of a system deploying a trained neural network to facilitate determination of dose distribution based on a radioactivity image according to some embodiments.

FIG. 1B illustrates system 100 to generate data indicative of radiation dose associated with a volume over a time period according to some embodiments. Similar to implementations of system 10, system 100 includes trained extrapolative neural network 110 which receives activity image 120 as input. Again, neural network 110 may comprise any type of neural network that is or becomes known, may utilize NALUs, and may be implemented using any suitable combination of hardware and/or software.

Neural network 110 outputs one or more time-activity curves 130. A time-activity curve plots the concentration of radioactive tracer in an ROI over time. Each of curves 130 may represent a different ROI within the imaged volume.

Network 110 may output each curve 130 as a set of points, each of which represents a respective time and a mean pixel value within an associated ROI at the respective time. Network 110 may output each curve 130 as data defining a function, where the data includes a set of parameters defining the form (or class) of the function and its variable coefficients. According to some embodiments, each time-activity curve 130 output by network 110 based on a particular activity image 120 belongs to a same function class (or shape) but is associated with different coefficients. The shape may be dependent upon the radioactive tracer which was used to acquire activity image 120.

Total dose estimation component 140 estimates a dose associated with each of curves 130 as is known in the art. Data 150 associates the total dose estimated for a curve 130 with the ROI represented by the curve 130.

According to some embodiments, an identifier of a radioactive tracer used to acquire image 120 and anatomical segmentation information are input to neural network 110 along with activity image 120. The anatomical segmentation information may assist network 110 in identifying organs within image 120, and the identifier may assist network 110 in determining the shape of a curve 130 associated with each organ.

Figure 2:
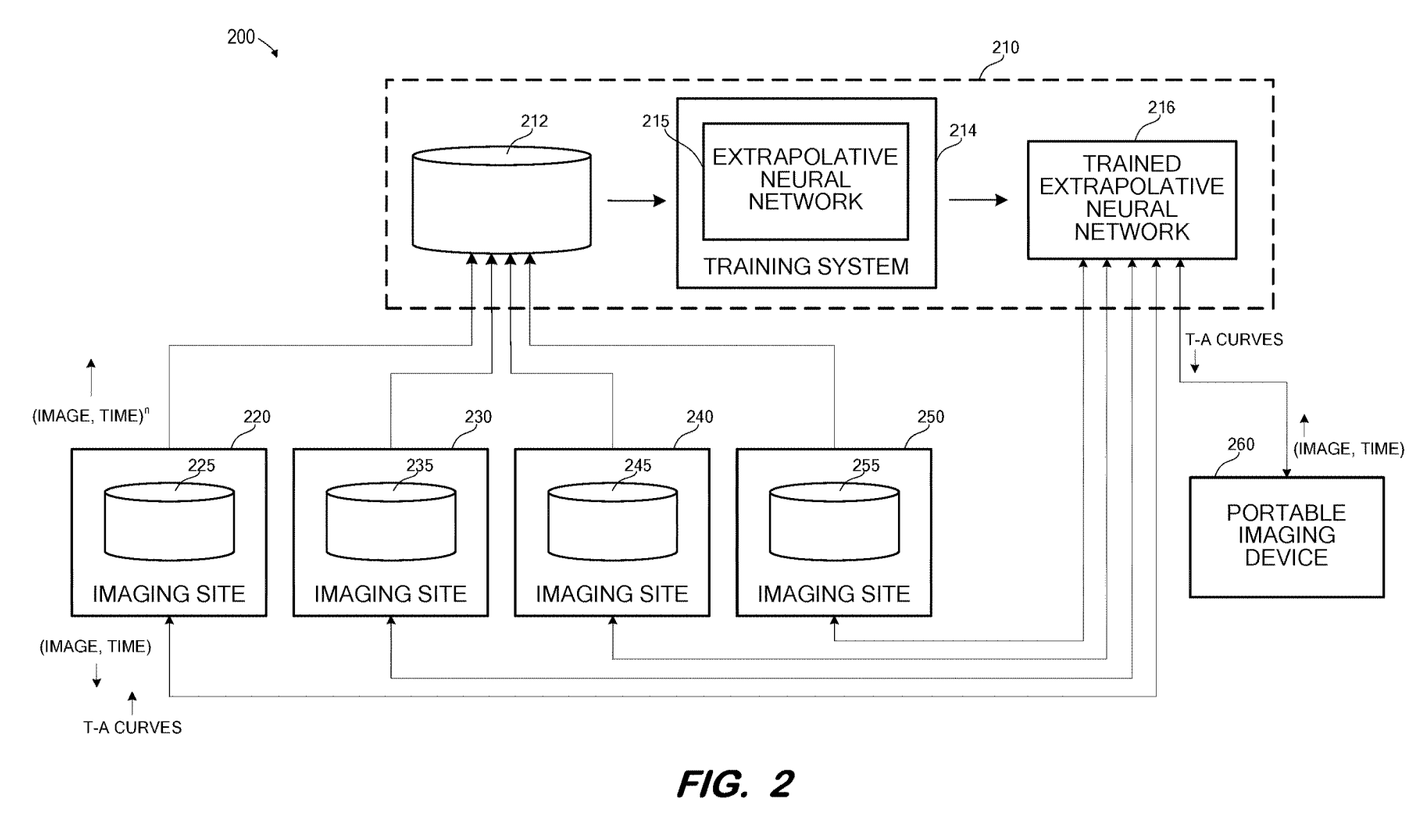
FIG. 2 is a block diagram of a system to train a neural network to determine one or more time-activity functions from a radioactivity image based on radioactivity images received from multiple imaging sites according to some embodiments.

FIG. 2 is a block diagram of system 200 to train a neural network to determine one or more time-activity functions from a radioactivity image based on radioactivity images received from multiple imaging sites according to some embodiments. Each component of system 200 may be implemented using any known combination of hardware and/or software, and one or more of the components may be implemented by a same computing system.

Network management system 210 comprises training data store 212, training system 214, extrapolative neural network 215, and trained extrapolative neural network 216. Training data store 212 may store training examples, each of which includes input data and associated ground truth data. The input data and ground truth data of a training example may comprise any suitable types of data, examples of which are provided herein.

Training system 214 generally operates to train the internal weights of extrapolative neural network 215 based on training data of training data store 212. As described above, extrapolative neural network 215 may include NALUs. Extrapolative neural network 215 may comprise an invertible neural network exhibiting a forward mapping and a reverse mapping, both of which are trained by training system 214. For example, the forward mapping may be optimized based on ground truths associated with each training example, and the backward mapping may be optimized to enforce biological and/or physical laws/constraints. In some embodiments, training system 214 trains extrapolative neural network 215 using reinforcement learning.

Trained extrapolative neural network 216 embodies weights learned during the aforementioned training. Generally, training results in the learning of functions which trained extrapolative neural network 216 applies to its inputs to generate an output. Trained extrapolative neural network 216 may comprise any suitable system for implementing such functions.

Trained extrapolative neural network 216 may operate as described above with respect to networks 11 and 110 described above. In the illustrated example of FIG. 2, each of imaging sites 220 through 250 and imaging device 260 may provide an activity image and a post-injection time associated with the activity image (as well as any other required inputs) to trained extrapolative neural network 216, which may be exposed as a Web service by system 210. Trained extrapolative neural network 216 applies its learned functions to the inputs to generate an output and returns the output. According to FIG. 2, the output comprises one or more time-activity curves, but embodiments are not limited thereto.

Imaging sites 220 through 250 may represent any locations at which activity images are acquired. One or more of imaging sites 220 through 250 may comprise a respective hospital or imaging center, and two or more of imaging sites 220 through 250 may comprise imaging theatres within a same hospital and/or imaging center. Each of data stores 225, 235, 245 and 255 represent activity images and associated data (e.g., acquisition time, tracer type, anatomical images) acquired at its respective imaging center.

As shown, imaging sites 220 through 250 provide activity images and associated data (e.g., acquisition time, tracer type, anatomical images) to system 210 for storage in data store 212 and use as training examples as described above. Such an arrangement may facilitate the acquisition of suitable amounts of training data.

As mentioned above, training examples are associated with ground truth data such as time-activity curves or dose information for one or more ROIs of each activity image. Such ground truth data for each training example may be determined at an associated imaging site and provided to system 210 or may be determined by system 210. In one example, imaging site 220 acquires projection images of radioactivity within a patient at each of several post-injection timepoints (e.g., 5 hrs, 4 hrs, 24 hrs, 48 hrs).

A three-dimensional activity image associated with each timepoint is reconstructed. Each three-dimensional activity image is segmented to identify various ROIs (e.g., organs and tumors) and the activity within each ROI. Segmentation may be assisted by a computed tomography (CT) image of the patient. A time-activity curve for each ROI is then generated based on the activity images.

Figure 3:
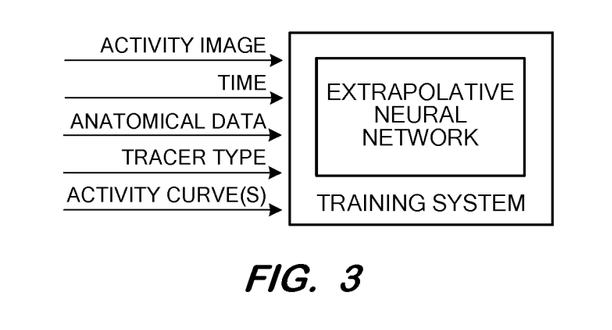
FIG. 3 is a block diagram illustrating training data for a neural network to determine one or more time-activity functions from a radioactivity image according to some embodiments.

Each three-dimensional activity image and its associated timepoint is provided to system 210 (along with, possibly, an identifier of the tracer and the CT image) as a training example, with the determined time-activity curves being ground truth data for each of the training examples. FIG. 3 is an example of a single training example being provided to a training system according to some embodiments. As shown, the training example includes an activity image, a post-injection image acquisition time, anatomical data (e.g., segmented CT image), a tracer type, and one or more associated activity curves.

Figure 4:
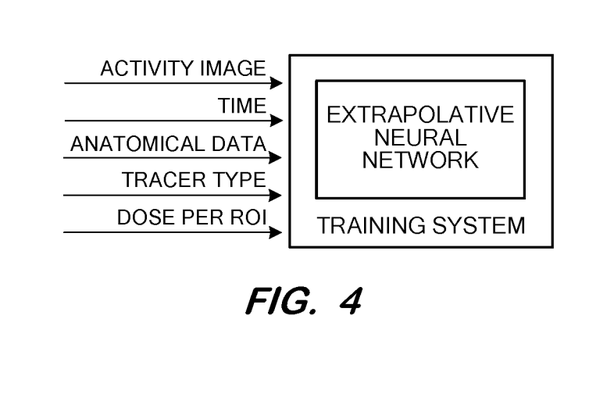
FIG. 4 is a block diagram illustrating training data for a neural network to determine one or more time-activity functions from a radioactivity image according to some embodiments.

In some embodiments, and with respect to system 10 of FIG. 1A, imaging site 220 may instead determine a dose associated with each ROI based on the time-activity curves. According to this example, the dose associated with each ROI is provided to system 210 as the ground truth data for each of the training examples. Extrapolative network 215 is therefore trained to output a dose per ROI rather than time-activity curves. FIG. 4 illustrates a training example according to this implementation. The training example includes an activity image, a post-injection image acquisition time, anatomical data (e.g., segmented CT image), a tracer type, and an estimated dose per ROI.

Some determinations attributed above to an imaging site may be performed by system 210 or training system 214. For example, system 210 or training system 214 may determine activity curves (or doses) based on received activity images and associate the determined activity curves (or doses) as ground truth data for the activity images. System 210 or training system 214 may also segment and label ROIs within the received activity images based on received CT data.

Portable imaging device 260 may comprise a low-resolution, low cost, and/or low power SPECT scanner or other device for generating activity images of a patient. Accordingly, activity images acquired by portable imaging device 260 might not be suitable for use as training examples. However, portable imaging device 260 may provide activity images to trained network 216, receive output time-activity curves therefrom as described above, and estimate a dose per ROI based on the time-activity curves.

According to some embodiments, the training and inference scenario depicted in FIG. 2 is regularly updating. That is, once training system 214 trains network 215 based on training examples received from sites 220 through 250 to result in trained network 216, data store 212 continues to collect and store training examples received from sites 220 through 250. After a particular number of new training examples has been received, or a particular time period has elapsed, or a command to refresh trained network 216 is received, for example, training system 214 again trains network 215 to generate new trained network 216. This training may be based on only training examples received since a last training, on all training examples received to-date, or on some combination thereof. New trained network 216 is then used to service inference requests received from sites 220 through 250, device 260, or any other client.

Network management system 210 may comprise one or more cloud-based servers and or storage systems to manage training and deployment of a neural network as described herein. A cloud-based implementation may provide resource elasticity and redundancy as is known in the art. A cloud-based implementation may facilitate communication with imaging sites as will be described below over secure Web protocols. Embodiments are not limited cloud-based implementations.

Figure 5:
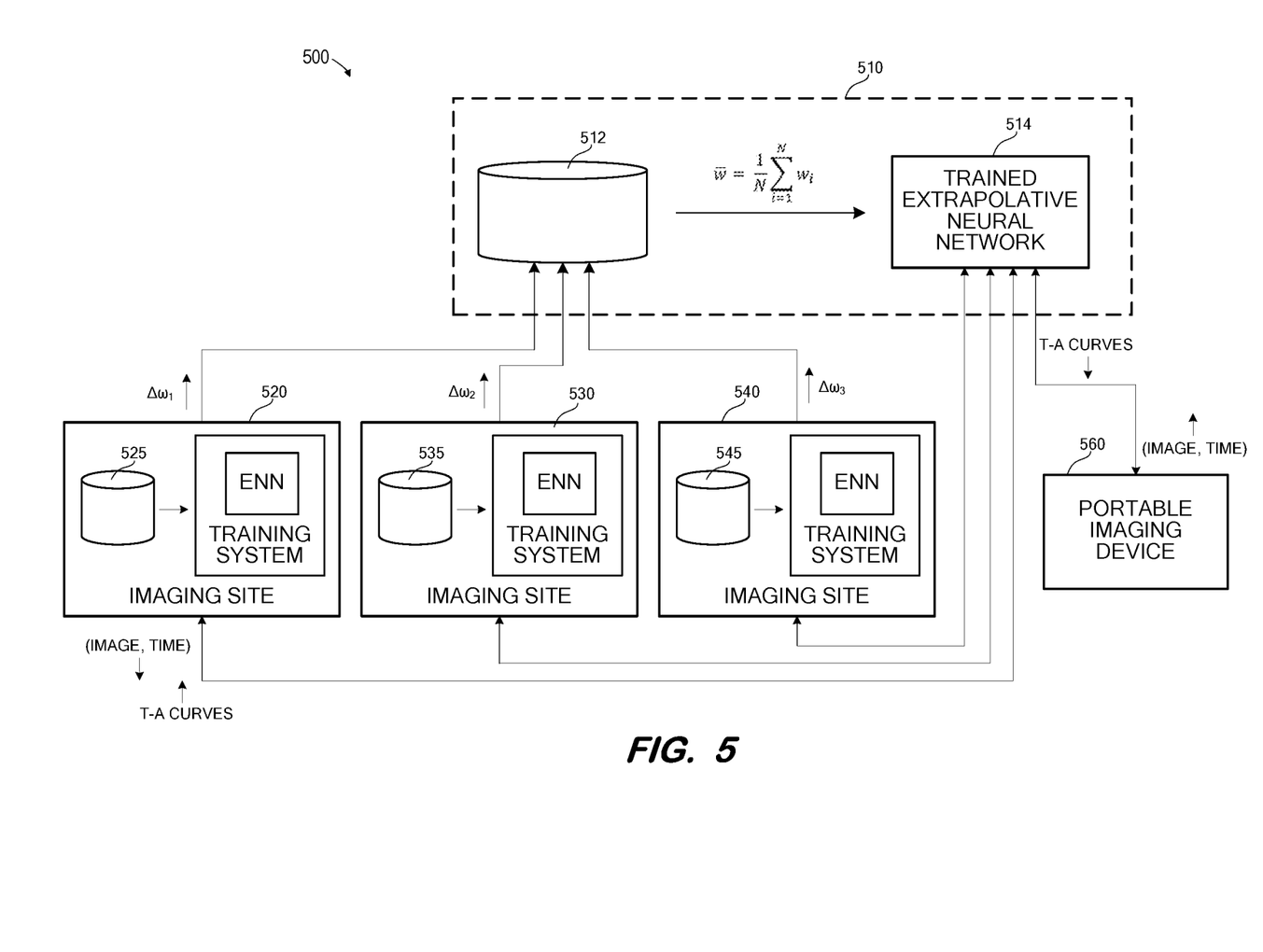
FIG. 5 is a block diagram of a system to generate a neural network to determine one or more time-activity functions from a radioactivity image based on network weights received from multiple imaging sites according to some embodiments.

FIG. 5 is a block diagram of system 500 to train a neural network to determine one or more time-activity functions from a radioactivity image based on trained network weights received from multiple imaging sites according to some embodiments. Each component of system 500 may be implemented using any known combination of hardware and/or software, and one or more of the components may be implemented by a same computing system.

In contrast to system 200, each of imaging sites 520, 530 and 540 provides respective network node weights to network management system 510 for storage in data store 512. By having imaging sites 520, 530 and 540 share node weights instead of activity images with system 510, system 500 may provide a greater degree of data privacy protection than system 200.

Each of imaging sites 520, 530 and 540 trains a same extrapolative neural network as described herein based on activity images and associated data acquired by the imaging site. Accordingly, each of imaging sites 520, 530 and 540 generates a respective trained extrapolative neural network based on its own activity images. The training methods employed by each of imaging sites 520, 530 and 540 need not be identical.

The weights of each trained network are extracted and transmitted to system 510. Since each trained network was trained based on activity images of its respective imaging site, the weights assigned to each node of each trained network will differ. As shown, imaging site 520 generates weights $\Delta\omega_1$, imaging site 530 generates weights $\Delta\omega_2$, and imaging site 540 generates weights $\Delta\omega_3$. Data store 512 collects the weights and system 510 uses the weights to implement trained extrapolative network 514, for example based on the following:

$$\overline{\omega} = \frac{1}{N}\sum_{i=1}^{N}\omega_i$$

where $\overline{\omega}$ is the weight assigned to a given node of trained extrapolative network 514, and N is the number of sites from which node weights are received. Any other algorithm for determining a node weight from several node weights may be employed.

Each of imaging sites 520, 530 and 540 and imaging device 560 may transmit an activity image and a post-injection time associated with the activity image (as well as any other required inputs) to trained extrapolative neural network 540, which may be exposed as a Web service by system 510. Trained extrapolative neural network 514 operates on the inputs based on its node weights to generate an output such as one or more time-activity curves, but embodiments are not limited thereto.

Figure 6:
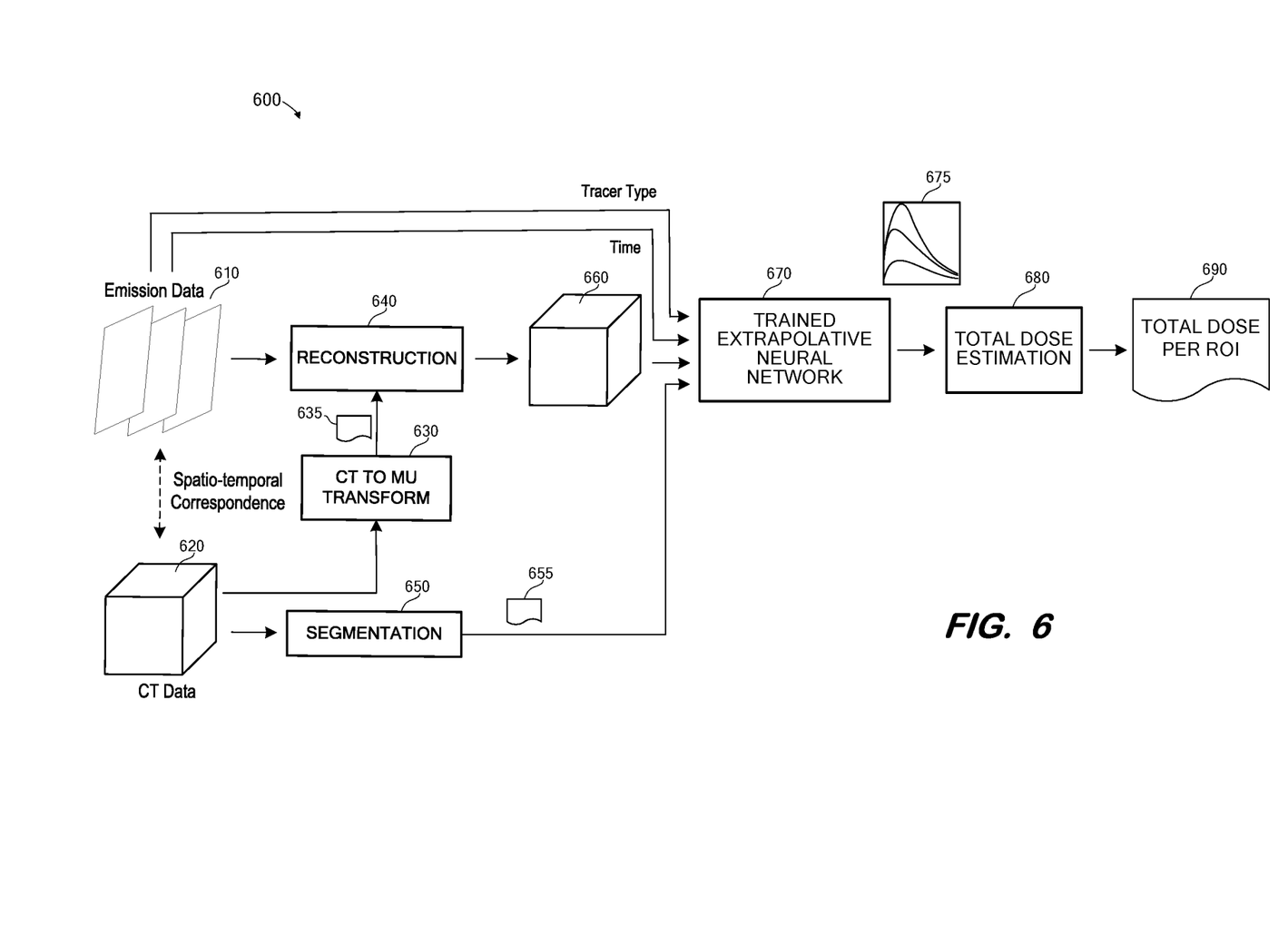
FIG. 6 is a block diagram of a system deploying a trained neural network to facilitate determination of dose distribution based on a radioactivity image according to some embodiments.

FIG. 6 is a block diagram of system 600 deploying a trained neural network to facilitate a determination of dose distribution based on a radioactivity image according to some embodiments. It is assumed that trained extrapolative neural network 670 has been trained to receive, as shown in FIG. 3, a three-dimensional activity image, a post-injection acquisition time, anatomical data (e.g., segmented CT data) and a tracer type.

Two-dimensional emission data 610 is generated by an emission imaging system during a scan of a subject. Such a system may comprise a SPECT system, a PET system, or another type of emission imaging system that is or becomes known. Emission data 610 may represent projection image data which is typically reconstructed into volumetric image data as is known in the art.

CT data 620 is acquired at the same time as, or shortly before or after, the acquisition off emission data 610. For example, CT data 620 may be acquired by a CT imaging system integrated with the SPECT system or PET system used to acquire emission data 610. Emission data 610 and CT data 620 may therefore be acquired while a patient remains in position on a table, thereby facilitating registration of emission data 610 and CT data 620.

According to emission imaging, an imaging source (e.g., a gamma ray-emitting radiopharmaceutical) internal to the subject (e.g., due to injection or ingestion thereof) emits source radiation (e.g., gamma rays) from within the subject to a detector. Absorption or scattering within the subject tissue attenuates the source radiation prior to reception of the source radiation by the detector. Images are created by determining the attenuation caused by the subject tissue. This determination is difficult in the case of emission imaging because the amount of radiation being emitted by the emission source(s) within the subject cannot be measured directly.

Therefore, in emission imaging, image reconstructions often incorporate attenuation corrections to generate visually-realistic and clinically-accurate images. The most-common attenuation corrections are based on Linear Attenuation Coefficient (LAC) maps ("mu-maps") derived from a CT scan of the subject tissue. Accordingly, CT-to-mu transform 630 converts CT data 620 to mu-map 635 of pixel-specific linear attenuation coefficients as is known in the art. Reconstruction component 640 receives mu-map 635 and emission data 610 and generates attenuation-corrected three-dimensional activity image 660 based thereon.

Moreover, segmentation component 650 performs a known segmentation process on CT data 620 to generate anatomical data 655. Anatomical data 655 may identify substantially homogeneous volumes within CT data 620 (and therefore within image 660) and identify such volumes as bone, specific organs, tumors, etc.

Trained extrapolative neural network 670 receives a tracer type, a post-injection acquisition time, three-dimensional activity image 660, and anatomical data 655. Based on the trained node weights thereof, network 670 outputs time-activity curves 675, each of which corresponds to a different ROI. As described with respect to FIG. 1B, total dose estimation unit 680 may then estimate total dose per ROI 690 in any manner that is or becomes known.

Figure 7:
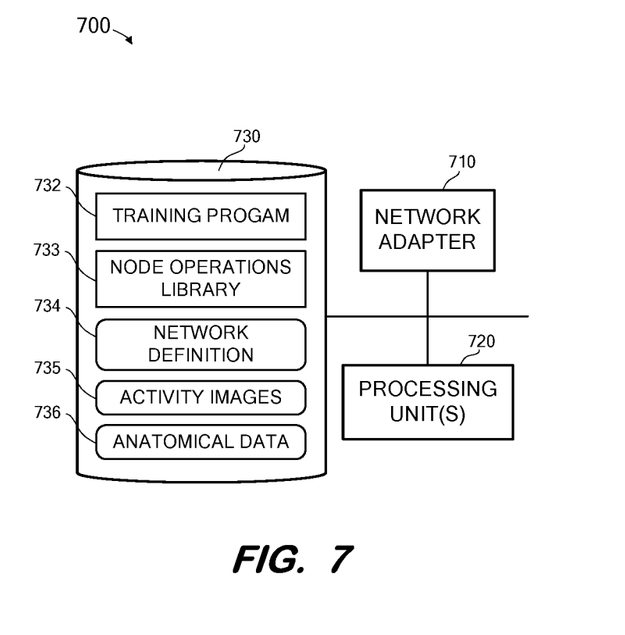
FIG. 7 is a block diagram of an apparatus to execute neural network training according to some embodiments.

FIG. 7 illustrates computing system 700 according to some embodiments. System 700 may comprise a computing system to facilitate the design and training of a network as is known in the art. Computing system 700 may comprise a standalone system, or one or more elements of computing system 700 may be located in the cloud.

System 700 includes network adapter 710 to communicate with external devices via a network connection. Processing unit(s) 720 may comprise one or more processors, processor cores, or other processing units to execute processor-executable program code. In this regard, storage system 730, which may comprise one or more memory devices (e.g., a hard disk drive, a solid-state drive), stores processor-executable program code of training program 732 which may be executed by processing unit(s) 720 to train a network as described herein.

Training program 732 may utilize node operations library 733, which includes code to execute various operations associated with node operations as defined in node operations library 733. According to some embodiments, computing system 700 provides interfaces and development software (not shown) to enable development of training program 732 and generation of network definition 734, such as a definition of an extrapolative neural network utilizing NALUs as described herein. Storage device 740 also includes activity images 735 and anatomical data 736 of various training examples, which may be received from disparate imaging sites as described above.

Figure 8:
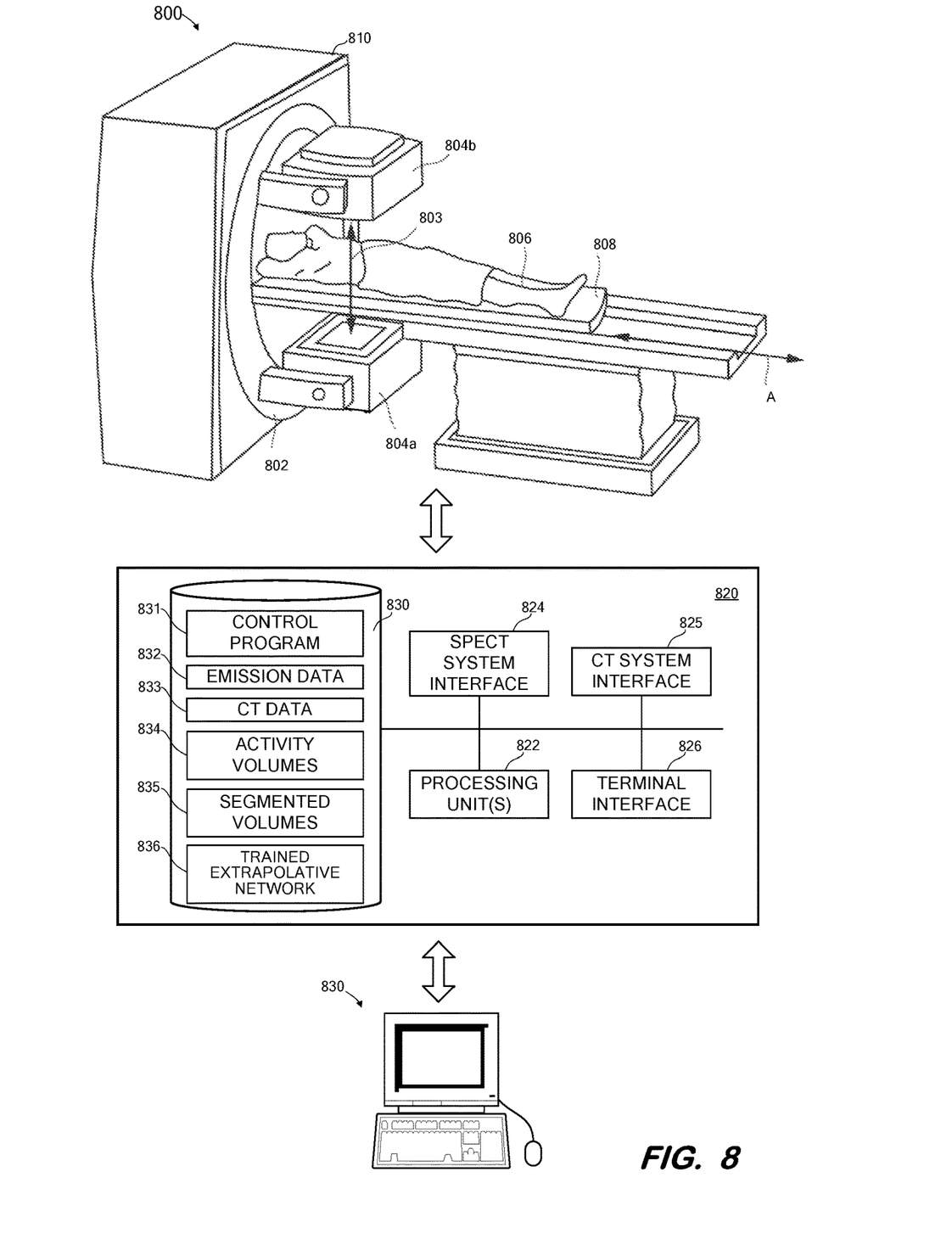
FIG. 8 illustrates an imaging system utilizing a trained neural network according to some embodiments.

FIG. 8 illustrates system 800 according to some embodiments. System 800 may comprise an implementation of system 600. System 800 is a SPECT/CT imaging system as is known in the art, but embodiments are not limited thereto. Each component of system 800 may include other elements which are necessary for the operation thereof, as well as additional elements for providing functions other than those described herein.

System 800 includes gantry 802 to which two or more gamma cameras 804a, 804b are attached, although any number of gamma cameras can be used. A detector within each gamma camera detects gamma photons (i.e., emission data) emitted by a radioactive tracer injected into the body of patient 806 lying on bed 808. Bed 808 is slidable along axis-of-motion A. At respective bed positions (i.e., imaging positions), a portion of the body of patient 806 is positioned between gamma cameras 804a, 804b in order to capture emission data from that body portion from various projection angles.

Housing 810 includes CT imaging elements. CT imaging elements comprise one or more pairs of opposed x-ray emitters and detectors. The CT imaging elements are mounted to rotate around patient 806 and acquire x-ray projection images thereof at multiple projection angles.

Control system 820 may comprise any general-purpose or dedicated computing system. Control system 820 includes one or more processing units 822 configured to execute processor-executable program code to cause system 820 to operate as described herein, and storage device 830 for storing the program code. Storage device 830 may comprise one or more fixed disks, solid-state random access memory, and/or removable media (e.g., a thumb drive) mounted in a corresponding interface (e.g., a USB port).

Storage device 830 stores program code of control program 831. One or more processing units 822 may execute control program 831 to, in conjunction with SPECT system interface 824, control motors, servos, and encoders to cause gamma cameras 804a, 804b to rotate along gantry 802 and to acquire two-dimensional emission data at defined imaging positions during the rotation. Similarly, control program 831 may be executed to, in conjunction with CT system interface 825, cause CT imaging elements within housing 810 to acquire two-dimensional x-ray images at defined imaging positions. The acquired emission data 832 and acquired CT data 833 may be stored in device 830.

Activity volumes 834 may be reconstructed from emission data 832, for example using mu-maps generated from CT data 833. Segmentation may be performed as described above to generated segmented volumes 835. Control program 831 may be executed to input an activity volume 834, a corresponding segmented volume 835, a post-injection acquisition time associated with the activity volume 834, and a corresponding tracer type to trained extrapolative network 836. Based on the inputs and the trained node weights thereof, network 836 outputs one or more time-activity curves or dose estimations.

Terminal 830 may comprise a display device and an input device coupled to system 820. Terminal 830 may receive and display any of one or more time-activity curves, dose estimations, activity volumes and/or segmented volumes, and may receive user input for controlling display of the data, operation of imaging system 800, and/or the processing described herein. In some embodiments, terminal 830 is a separate computing device such as, but not limited to, a desktop computer, a laptop computer, a tablet computer, and a smartphone.

Those in the art will appreciate that various adaptations and modifications of the above-described embodiments can be configured without departing from the claims. Therefore, it is to be understood that the claims may be practiced other than as specifically described herein.

What is claimed is:

1. A system comprising:
    a storage device; and
    a processor to execute processor-executable program code stored on the storage device to cause the system to:
        acquire a plurality of images, each of the plurality of images representing radiotracer concentration in a respective volume at a respective time period;
        train a neural network, based on the plurality of images, to generate a first time-activity curve associated with a first volume over a first time period based on a first image representing radiotracer concentration in the first volume over a second time period, the second time period being shorter than the first time period; and
        determine a first radiation dose associated with the first volume over the first time period based on the first time-activity curve.

2. A system according to claim 1, wherein training of the neural network comprises training of the neural network to generate a second time-activity curve associated with a second volume, and
    wherein the processor to execute processor-executable program code stored on the storage device to cause the system to determine a second radiation dose associated with the second volume over the first time period based on the second time-activity curve.

3. A system according to claim 1, wherein a first plurality of the plurality of images are acquired from a first imaging site, and wherein a second plurality of the plurality of images are acquired from a second imaging site.

4. A system according to claim 3, the processor to execute processor-executable program code stored on the storage device to cause the system to:
    acquire a third plurality of images from the first imaging site, each of the third plurality of images representing radiotracer concentration in a respective volume at a respective time period;
    acquire a fourth plurality of images from the second imaging site, each of the fourth plurality of images representing radiotracer concentration in a respective volume at a respective time period; and
    re-train the neural network, based on the third plurality of images and the fourth plurality of images, to generate a first time-activity curve associated with a first volume over a first time period based on a first image representing radiotracer concentration in the first volume over a second time period shorter than the first time period.

5. A system according to claim 1, wherein each of the plurality of images is associated with a tracer type, a post-injection time period, anatomical data, and wherein training of the neural network comprises:
    inputting the tracer type, the post-injection time period, and anatomical data, associated with each of the plurality of images into the neural network.

6. A system according to claim 1, wherein the neural network comprises neural arithmetic logic units.

7. A system comprising:
    a scanner to acquire a plurality of projection images indicating a degree of radioactivity emitted from locations of a volume over a first time period; and
    a processor to:
    reconstruct a first three-dimensional image indicating a degree of radioactivity emitted from locations of the volume based on the plurality of projection images;
    input the first three-dimensional image to a neural network to generate a time-activity curve associated with the volume over a second time period longer than the first time period; and
    determine a radiation dose associated with the volume over the first time period based on the time-activity curve.

8. A system according to claim 7, wherein the time-activity curve comprises a first time-activity curve associated with a first sub-volume of the volume and a second time-activity curve associated with a second sub-volume of the volume, and
    wherein the radiation dose associated with the volume comprises a first radiation dose associated with the first sub-volume and a second radiation dose associated with the second sub-volume.

9. A system according to claim 7, further comprising:
    a second scanner to acquire a plurality of x-ray projection images of the volume,
    wherein the processor is to:
    reconstruct a second three-dimensional image from the plurality of x-ray projection images; and
    generate a linear attenuation coefficient map based on the second three-dimensional image,
    wherein reconstruction of the first three-dimensional image is based at least in part on the linear attenuation coefficient map.

10. A system according to claim 9, the processor further to:
    segment the second three-dimensional image to generate anatomical data,
    wherein the anatomical data is input to the neural network with the first three-dimensional image.

11. A system according to claim 10, wherein the first time period is input to the neural network with the first three-dimensional image and the anatomical data.

12. A method comprising:
    acquiring a plurality of projection images indicating a degree of radioactivity emitted from locations of a volume over a first time period;

reconstructing a first three-dimensional image indicating a degree of radioactivity emitted from locations of the volume based on the plurality of projection images;
inputting the first three-dimensional image to a neural network to generate a time-activity curve associated with the volume over a second time period; and
determining a radiation dose associated with the volume over the first time period based on the time-activity curve,
wherein the second time period is longer than the first time period.

13. A method according to claim 12, wherein the time-activity curve comprises data representing a first time-activity curve associated with a first sub-volume of the volume and a second time-activity curve associated with a second sub-volume of the volume, and
wherein the radiation dose associated with the volume comprises a first radiation dose associated with the first sub-volume and a second radiation dose associated with the second sub-volume.

14. A method according to claim 12, further comprising:
acquiring a plurality of x-ray projection images of the volume;
reconstructing a second three-dimensional image from the plurality of x-ray projection images; and
generating a linear attenuation coefficient map based on the second three-dimensional image,
wherein reconstructing the first three-dimensional image is based at least in part on the linear attenuation coefficient map.

15. A method according to claim 14, further comprising:
segmenting the second three-dimensional image to generate anatomical data,
wherein the anatomical data is input to the neural network with the first three-dimensional image.

16. A method according to claim 15, wherein the first time period is input to the neural network with the first three-dimensional image and the anatomical data.

* * * * *